United States Patent [19]

Hodge

[11] Patent Number: 4,751,239
[45] Date of Patent: Jun. 14, 1988

[54] 6' CARBONATE ESTERS OF ZEARALANOL AND ITS DERIVATIVES

[75] Inventor: Edward B. Hodge, Terre Haute, Ind.

[73] Assignee: International Minerals & Chemical Corp., Terre Haute, Ind.

[21] Appl. No.: 67,532

[22] Filed: Jun. 29, 1987

[51] Int. Cl.$^4$ .................. A61K 31/365; C07D 313/00
[52] U.S. Cl. ...................................... 514/450; 549/270
[58] Field of Search ......................... 549/270; 514/450

[56] References Cited

U.S. PATENT DOCUMENTS

| | | | |
|---|---|---|---|
| 3,196,019 | 7/1965 | Andrews et al. | 549/270 |
| 3,239,341 | 3/1966 | Hodge et al. | 549/270 |
| 3,239,345 | 3/1966 | Hodge et al. | 549/270 |
| 3,239,346 | 3/1966 | Hodge et al. | 549/270 |
| 3,239,348 | 3/1966 | Hodge et al. | 549/270 |
| 3,239,354 | 3/1966 | Hodge et al. | 549/270 |
| 3,860,616 | 1/1975 | Hoffsommer et al. | 260/343 |
| 4,088,658 | 5/1978 | Robertson | 549/270 |
| 4,409,392 | 10/1983 | Hodge | 549/270 |
| 4,443,470 | 4/1984 | Hodge et al. | 549/270 |

OTHER PUBLICATIONS

Hidy et al., "Zearalenone and Some Derivatives: Production and Biological Activites", Adv. Appl. Microbiol., 22:59-82, (1977).

Shipchandler, "Chemistry of Zearalanone and Some of Its Derivatives", Heterocycles, 3(6):471-520, (1975).

Peters et al., "A Stereoselective Synthetic Route to (R)-Zearalanone", J. Med. Chem., vol. 18, No. 2, 215-217, (1975).

Primary Examiner—Jane T. Fan
Attorney, Agent, or Firm—Wendell Ray Guffey; Thomas L. Farquer

[57] ABSTRACT

6' carbonate esters of zearalanol and its derivatives are used to promote growth in ruminants. The compounds have the structural formula:

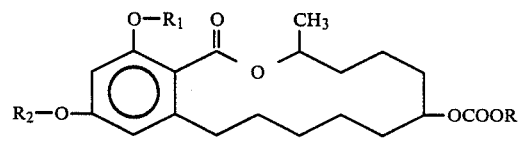

wherein $R_1$ and $R_2$, which may be the same or different, are H, X, or COX, where X is an alkyl group having from 1-6 carbon atoms; and R is an alkyl group or a Br or Cl substituted alkyl group having from 1-12 carbon atoms.

20 Claims, No Drawings

6' CARBONATE ESTERS OF ZEARALANOL AND ITS DERIVATIVES

This invention relates generally to Resorcylic Acid Lactone (RAL) derivatives and particularly to 6–carbonate esters of zearalanol and its derivatives which are useful for promoting growth in ruminants.

BACKGROUND OF THE INVENTION

Zearalenone and its derivatives are the basic Resorcylic Acid Lactone (RAL) compounds used as the starting materials for the compounds of the present invention. Zearalenone may be prepared by culturing the zearalenone producing strain of *Gibberella zeae* as taught in U.S. Pat. No. 3,196,019, incorporated herein by reference. Zearalenone and its ring-opened and other derivatives have been reviewed in the literature. Shipchandler, *Heterocycles*, 3(6):471–520 (1975) and Hidy et al "Zearalenone and Some Derivatives: Production and Biological Activities", *Adv. Appl. Microbiol.*, 22:59–82 (1977).

Zearalenone has been chemically modified to form numerous derivatives. U.S. Pat. No. 3,239,348, incorporated herein by reference, discloses a method for producing zearalenol from zearalenone by reducing the ketone carbonyl group. U.S. Pat. No. 3,239,345, incorporated herein by reference, discloses a method for producing zearalanol from zearalenone and zearalenol by reducing the ketone carbonyl group and/or the macrocylic ring double bond.

These compounds have generally been used to improve growth performance in ruminants and to reduce the severity of vasomotor symptoms associated with menopause in women. These compounds, however, have often been difficult to administer or have had undesirable side effects. In addition, these compounds have often not been as highly effective for the intended purpose as desirable. There is, therefore, a continuing need for new compounds that can reduce problems with administration, lessen the toxic and other undesirable side effects, and improve upon the efficacy of such compounds. One method for meeting these needs has been to produce various derivatives, particularly ester derivatives or compounds that give a biological response similar to the ester derivatives, of the compounds in an effort to improve the efficacy of the compound and lessen any possible side effects.

SUMMARY OF THE INVENTION

It is, therefore, an object of the present invention to provide 6' carbonate esters of zearalanol and its derivatives.

It is another object of the present invention to provide a method for promoting growth in ruminants by administering to the ruminants a growth promoting amount of 6' carbonate esters of zearalanol and its derivatives.

It is another object of the present invention to provide a composition containing 6' carbonate esters of zearalanol and its derivatives.

These and other objects are achieved by synthesizing 6' carbonate esters of zearalanol and its derivatives and administering the compounds to ruminants to promote growth. The compounds of the present invention have the structure:

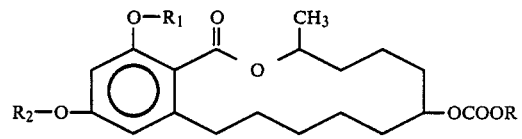

wherein $R_1$ and $R_2$ which may be the same or different, are H, X, or COX, where X is an alkyl group having from 1-6 carbon atoms; and R is an alkyl group or a Br or Cl substituted alkyl group having from 1-12 carbon atoms.

Preferably, $R_1$ and $R_2$ are H or $COCH_3$; and R is an alkyl group or a Br or Cl substituted alkyl group having from 1-6 carbon atoms. Most preferably, $R_1$ and $R_2$ are H; and R is $CH_3$, $C_2H_5$, $C_3H_7$, $C_4H_9$, or $CH_2CZ_3$, wherein Z is Br or Cl.

Other objects, advantages, and novel features of the present invention will become apparent from the following detailed description of the invention.

DETAILED DESCRIPTION OF THE INVENTION

In accordance with the present invention, 6' carbonate esters of zearalanol and its derivatives are synthesized and used to promote growth in ruminants. The compounds have the following structural formula:

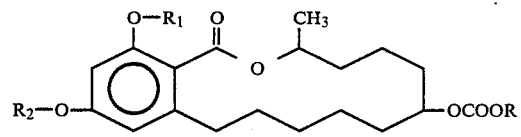

Wherein $R_1$ and $R_2$, which may be the same or different, are H, X, or COX, where X is an alkyl group having from 1-6 carbon atoms; and R is an alkyl group or a Br or Cl substituted alkyl group having from 1-12 carbon atoms.

Preferably, $R_1$ and $R_2$ are H or $COCH_3$; and R is an alkyl group or a Br or Cl substituted alkyl group having from 1-6 carbon atoms.

Most preferably, $R_1$ and $R_2$ are H; and R is $CH_3$, $C_2H_5$, $C_3H_7$, $C_4H_9$, or $CH_2CZ_3$, wherein Z is Br or Cl.

The amount of compound of the present invention administered may vary depending upon the particular type, maturity, and the size of the ruminant. Generally, the compounds according to the present invention are administered to the ruminant in dosages of from 0.01-0.50 mg/kg of body weight, preferably from 0.1-0.3 mg/kg of body weight.

The compounds of the present invention can be administered as the compound or as a pharmaceutically acceptable salt of the compound, alone, in combination, or in combination with pharmaceutically acceptable carriers, diluents, and vehicles. The carrier can be an antibiotic, other growth promoting agent, an inert carrier, and the like. Most preferably, the compounds of the present invention are mixed with a pharmaceutically acceptable carrier to form a composition which allows for easy dosage preparation and administration.

The compounds of the present invention can be administered to ruminants by any suitable method including orally, by injection, using an implant, and the like. Oral administration includes administering the compounds of the present invention in tablets, suspensions, implants, solutions, emulsions, capsules, powders, syrups, boluses, feed compositions, and the like. Injections and implants are preferred because they permit precise control of the timing and dosage levels used for administration, with implants being most preferred. The compounds of the present invention are preferably administered parenterally. Such administration may be by intravenous or intramuscular injection, intraperitoneal injection, or subcutaneous implant.

The compounds according to the present invention can be administered to the ruminant in the form of a slow-release subcutaneous implant which is inserted beneath the skin of the ruminant, preferably in the ear for large animals. The implant can take the form of a pellet which slowly dissolves after being implanted in the ruminant or a biocompatible and compound compatible delivery module well known to those skilled in the art. Such well known dosage forms are designed such that the active ingredients are slowly released over a period of several days to several weeks. The implant is designed to deliver from about 0.15–8.5 µg/kg of body weight/day, preferably from about 1.5–5.0 µg/kg of body weight/day.

When given by injection, the compounds of the present invention can be administered to the ruminants with any biocompatible and compound compatible carrier such as various vehicles, adjuvants, additives, and diluents to achieve a composition usable as a dosage form. The compounds of the present invention are added to the carrier in amounts sufficient to supply from about 0.02–0.5 mg/kg of body weight to the ruminant when injected. Preferably, the compounds of the present invention are added to a oil vehicle in amounts sufficient to supply from about 0.1–0.3 mg/kg of body weight.

Aqueous vehicles such as water having no nonvolatile pyrogens, sterile water, and bacteriostatic water are also suitable to form injectable compound compositions. In addition, several other aqueous vehicles can be used. These include isotonic injection compositions that can be sterilized such as Ringer's, dextrose, dextrose and sodium chloride, and lactated Ringer's. Addition of water-miscible solvents, such as methanol, ethanol, or propylene glycol generally increases solubility of the compounds in these vehicles.

Nonaqueous vehicles such as cottonseed oil, sesame oil, or peanut oil and esters such as isopropyl myristate may also be used as solvent systems for compound compositions. Additionally various additives which enhance the stability, sterility, and isotonicity of the composition including antimicrobial preservatives, antioxidants, chelating agents, and buffers can be added. Any vehicle, diluent, or additive used would, however, have to be compatible with the compounds of the present invention.

The compounds according to the present invention can be administered orally to the ruminant. For example, the compounds of the present invention can be blended with ordinary feed compositions in amounts sufficient to promote growth. When the compounds of the present invention are to be administered in feeds, a ruminant feed composition may be prepared containing the usual nutritionally-balanced feed containing quantities of carbohydrates, proteins, vitamins and minerals, together with the compounds in accordance with the present invention. Some of the usual dietary elements included in ruminant feed compositions are grains, such as ground grain and grain byproducts, animal protein substances, such as those found in fish meal and meat scraps, vegetable proteins, like soybean oil meal or peanut oil meal; vitamins and vitamin-containing materials, e.g., vitamin A and D mixtures, riboflavin supplements and other vitamin B complex members; and bone meal and limestone to provide minerals. A type of conventional feed material for use with cattle includes alfalfa hay and ground corncobs together with supplementary vitamins and vitamin-containing substances if desired. The compounds according to the present invention are admixed with the feed in amounts sufficient to supply from about 0.01–0.50 mg/kg body weight, typically 0.4–20 grams/ton of feed, to the ruminant.

The compounds of the present invention are useful as growth promotants in ruminants. In addition, the compounds can be used in post-menopausal replacement therapy.

Although not wishing to be bound by theory, it is believed that the carbonate derivatives of the present invention are cleaved in vivo to form the corresponding alcohol. For example, carbonates of zearalanol are hydrolyzed in vivo to form zearalanol. The parent compound, zearalanol in the example, effects the desired growth promotion or other effect. A significant advantage is achieved by administering the derivative instead of parent compound; the derivative is not cleared by the body as fast as is the parent compound thus allowing the growth promoting effect to be extended over a longer period. This increases the amount of growth promotion produced by a given amount of compound, reduces the amount of compound that must be administered to achieve the desired growth promotion, and decreases the number of dosages that must be administered in a given time.

The invention having been generally described, the following examples are given as particular embodiments of the invention and to demonstrate the practice and advantages thereof. U.S. Pat. Nos., 3,196,019, 3,239,345, and 3,239,348, incorporated herein by reference, disclose methods for producing zearalenone, zearalenol, zearalanol, and various esters and other derivatives of these compounds. These compounds and their derivatives are used to produce the compounds of the present invention. It is understood that the examples are given by way of illustration and are not intended to limit the Specification or the claims to follow in any manner. In particular, the Specification and claims as written are intended to include all isomers of the compounds and the alkyl groups are intended to include linear and branched chains.

EXAMPLE 1

Preparation of Methyl 6'-Zearalanol Carbonate

To 5.4 g of 2,2,2-trichloroethyl 2,4-diacetyl-6'-zearalanol carbonate, in 100 ml of methanol was added 1.1 g of sodium methoxide. After 3½ h the solution was added to 600 ml of water and the mixture was acidified with dilute hydrochloric acid. Crystals formed which were filtered and dried to give 3.2 g, M.P. 133°–140° C. This was crystallized from 50 ml of cyclohexane plus 2.5 ml of 2-propanol to give 2.6 g, M.P. 138°–141.5° C. Analysis - calculated for $C_{20}H_{28}O_7$: C–63.14%, H–7.42%; found: C–62.77%, H–7.22%. The proton NMR was consistent with the above structure, and the molecular weight of 380 was confirmed by mass spectrometry.

EXAMPLE 2

Preparation of Ethyl 6'-Zearalanol Carbonate

To 5.0 g of 2,2,2-trichloroethyl 2,4-diacetyl-6'-zearalanol carbonate in 100 ml of warm ethanol was added 0.7 g of sodium hydroxide. The mixture was stirred for 30 min, then mixed with 200 ml of water and acidified with dilute hydrochloric acid. A crystalline precipitate formed. This was filtered and air dried. There were 3.2 g, M.P. 159°-166° C. Added most of the crystals to 25 ml of cyclohexane, heated to boiling and then added 2-propanol slowly to the boiling mixture until solution was almost complete. Filtered hot, cooled filtrate for one hour, then filtered. After air drying overnight there were 2.2 g M.P. 160°-166° C. Analysis: calculated for $C_{21}H_{30}O_7$: C-63.94%, H-7.67%, O-28.39%; found: C-63.79%, H-7.63%, O-28.43%. Proton NMR was consistent with the above structure and the molecular weight of 394 was confirmed by mass spectrometry.

EXAMPLE 3

Preparation of 2,2,2-Trichloroethyl 2,4-Diacetyl-6'-Zearalanol Carbonate

To 10 g of zearalanol 2,4-diacetate in 50 ml of dry pyridine added slowly 5.5 g of 2,2,2-trichloroethyl chloroformate. A waxy precipitate formed which slowly dissolved on stirring, being replaced by a small crystalline precipitate. The mixture was left for 48 h, then mixed with 300 ml of ice water. A gum was formed which slowly crystallized. The aqueous layer was poured off, and the solid was washed with water, (3×100 ml). The solid was recrystallized once from 100 ml of 2-propanol, then twice from 50 ml of ethanol. This gave 7.8 g, M.P. 93°-98° C. Analysis calc. for $C_{25}H_{31}Cl_3O_9$ (581.88): C-51.60%, H-5.37%, O-24.75%, Cl-18.28%. Found: C-51.59%, H-5.52%, O-24.62%, Cl-18.22%. The correct molecular weight was shown by mass spectrometry.

EXAMPLE 4

Preparation of 2,2,2-Trichloroethyl6'-Zearalanol Carbonate

To 50 ml of acetone was added 5.8 g (0.01 mole) of 2,2,2-trichloroethyl 2,4-diacetyl-6'-zearalanol carbonate and then 1.8 g (0.02 mole) of morpholine. The next day the solution was mixed with 300 ml of water and acidified with dil. hydrochloric acid. A gum came out. The next day the gum was found to have crystallized. This was recrystallized 3 times from 30 ml of nitromethane. The melting point was 91°-113°-117° C. One further crystallization from 100 ml of cyclohexane gave 1.3 g, M.P. 125°-26° C. analysis: calc. for $C_{21}H_{27}Cl_3O_7$: C-50.66%, H-5.47%, Cl-21.37%, O-22.50%. Found: C-50.93%, H-5.58%, Cl-20.65%, O-22.35%. The molecular weight was confirmed by mass spectrometry.

EXAMPLE 5

Preparation of Butyl 2,4-Diacetyl6'-Zearalanol Carbonate

To 50 ml of dry pyridine were added 10 g of zearalanol 2,4-diacetate and then 3.4 g of butyl chloroformate. After 48 h at room temperature the mixture was added to 300 ml of ice water. A gum formed. The aqueous layer was poured off, the gum was washed with water (2×300 ml) and then dissolved in 20 ml of 3A-denatured ethanol. To this solution was added 5 ml of water and the solution was put in the refrigerator. Three days later this was filtered. To the precipitate was added 1.3 g from a previous preparation and the mixture was crystallized from 35 ml of 3A-denatured ethanol plus 8 ml of water. This gave 5.3 g, M.P. 66°-70° C. Analysis calculated for $C_{27}H_{38}O_9$ (506.571): Cl 64.01%, H-7.56%, O-28.43%; found: C-63.76%, H-7.63%, O-28.69%. The molecular weight was confirmed by mass spectrometry.

EXAMPLE 6

The uterotropic activity screening test was conducted in young adult female mice (CF1 strain) weighing 19-24 g each, purchased from Engle's Laboratory Animals, Farmersburg, Indiana. The test mice were ovariectomized and held for two weeks to allow for depletion of natural estrogens.

The tests were conducted by administering to groups of mice, a selected total dose of test material divided into three consecutive days. Positive and negative control groups were also tested for comparison. On the fourth day, all mice were sacrificed, body weights were made and recorded, the uterus of each mouse removed, weighed and recorded. Average body and uterine weights were calculated. For comparison, the percent uterine weight to body weight was determined.

Uterotropic activity was indicated when the percent uterine weight to body weight in a test group was greater than that of a negative control group. Uterotropic activity of a test material may then be compared to that of a known estrogenic material. The results are shown in Table 1.

Referring to Table 1, the carbonate compounds of the present invention are more estrogenic than zearalanol when administered by injection.

TABLE 1

| 6'-Carbonates of Zearalanol | | | | | |
|---|---|---|---|---|---|
| $R_1$ | $R_2$ | R | M.P. | IP[1] | Oral[1] |
| H | H | $CH_3$ | 138-141.5 | 2.0 | 0.9 |
| H | H | $C_2H_5$ | 160-166 | 2.5 | 0.7 |
| H | H | $C_4H_9$ | 108-111 | 3.4 | 1.0 |
| H | H | $CH_2CCl_3$ | 125-126 | 2.8 | 0.8 |
| $COCH_3$ | $COCH_3$ | $C_4H_9$ | 66-70 | | |
| $COCH_3$ | $COCH_3$ | $CH_2CCl_3$ | 93-98 | 3.0 | 0.8 |

[1]Approximate mouse uterotropic value relative to zearalanol obtained by dividing the increase in uterine weight by the increase from zearalanol; both at 100 μg total dose.

I claim:

1. A compound having the formula:

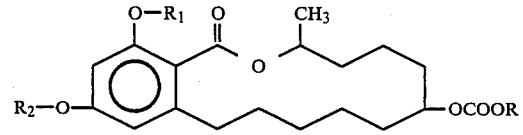

wherein $R_1$ and $R_2$, which may be the same or different, are H, X, or COX, where X is an alkyl group having from 1-6 carbon atoms; and R is an alkyl group or a Br or Cl substituted alkyl group having from 1-12 carbon atoms.

2. The compound of claim 1 wherein $R_1$ and $R_2$ are H or $COCH_3$; and R is an alkyl group or a Br or Cl substituted alkyl group having from 1-6 carbon atoms.

3. The compound of claim 1 wherein $R_1$ and $R_2$ are H; and R is $CH_3$, $C_2H_5$, $C_3H_7$, $C_4H_9$, or $CH_2CZ_3$, wherein Z is Br or Cl.

4. A method for promoting growth in a ruminant comprising the step of:

administering to said ruminant a growth promoting amount of a compound having the formula:

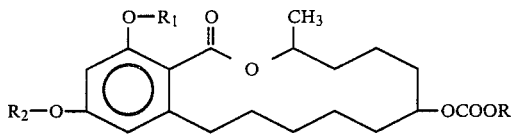

wherein $R_1$ and $R_2$, which may be the same or different, are H, X, or COX, where X is an alkyl group having from 1-6 carbon atoms; and R is an alkyl group or a Br or Cl substituted alkyl group having from 1-12 carbon atoms.

5. The method of claim 5 wherein $R_1$ and $R_2$ are H or $COCH_3$; and R is an alkyl group or a Br or Cl substituted alkyl group having from 1-6 carbon atoms.

6. The method of claim 5 wherein $R_1$ and $R_2$ are H; and R is $CH_3$, $C_2H_5$, $C_3H_7$, $C_4H_9$, or $CH_2CZ_3$, wherein Z is Br or Cl.

7. The method of claim 4 wherein said compound is administered in an amount from about 1-20 mg/kg of body weight.

8. The method of claim 4 wherein said compound is administered orally, said oral method selected from the group consisting of administering said compound to said ruminants in tablets, suspensions, solutions, emulsions, capsules, powders, syrups, boluses, and feed compositions.

9. The method of claim 4 wherein said compound is administered in a feed composition, said feed composition further comprising:

a nutritionally balanced feed; and a growth promoting amount of at least one of said compound admixed with said feed.

10. The method of claim 4 wherein said compound is administered by injecting a composition, said composition further comprising:

a biocompatible and compound compatible vehicle; and a growth promoting amount of said compound admixed with said composition.

11. The method of claim 10 wherein said vehicle is an oil vehicle.

12. The method of claim 4 wherein said compound is administered using an implant, said implant further comprising:

a biocompatible and compound compatible implant material; and a growth promoting amount of said compound admixed with said implant material.

13. A composition suitable for promoting growth in a ruminant comprising:

a compound having the formula:

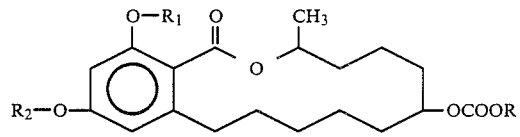

wherein $R_1$ and $R_2$, which may be the same or different, are H, X, or COX, where X is an alkyl group having from 1-6 carbon atoms; and R is an alkyl group or a Br or Cl substituted alkyl group having from 1-12 carbon atoms; and an inert pharmaceutical carrier.

14. The composition of claim 13 wherein $R_1$ and $R_2$ are H or $COCH_3$; and R is an alkyl group or a Br or Cl substituted alkyl group having from 1-6 carbon atoms.

15. The composition of claim 13 wherein $R_1$ and $R_2$ are H; and R is $CH_3$, $C_2H_5$, $C_3H_7$, $C_4H_9$, or $CH_2CZ_3$, wherein Z is Br or Cl.

16. The composition of claim 13 wherein the amount of said compound in said composition is an amount sufficient to supply from about 1-20 mg/kg body weight to said ruminant.

17. The composition of claim 13 wherein said composition is an injectable composition suitable for promoting growth in ruminants further comprising:

a biocompatible and compound compatible vehicle; and a growth promoting amount of said compound admixed with said vehicle.

18. The composition of claim 17 wherein said vehicle is an oil vehicle.

19. The composition of claim 13 wherein said composition is a feed composition suitable for promoting growth in ruminants further comprising:

a nutritionally balanced feed; and a growth promoting amount of said compound admixed with said feed.

20. The composition of claim 13 wherein said composition is an implant suitable for promoting growth in ruminants further comprising:

a biocompatible implant material; and a growth promoting amount of said compound admixed with said implant material.

* * * * *